(12) United States Patent
Chen et al.

(10) Patent No.: US 12,144,493 B2
(45) Date of Patent: Nov. 19, 2024

(54) COLLECTION AND TEST DEVICE FOR RAPID TEST

(71) Applicant: NATIONAL DEFENSE MEDICAL CENTER, Taipei (TW)

(72) Inventors: Jia-En Chen, Taipei (TW); Juin-Hong Cherng, Taipei (TW); Yuan-Hao Chen, Taipei (TW); Cheng-Che Liu, Taipei (TW); Cheng-Cheung Chen, Taipei (TW); Yu-Min Tsai, Taipei (TW); Chin-Hsieh Yi, Taipei (TW)

(73) Assignee: NATIONAL DEFENSE MEDICAL CENTER, Taipei (TW)

( * ) Notice: Subject to any disclaimer, the term of this patent is extended or adjusted under 35 U.S.C. 154(b) by 329 days.

(21) Appl. No.: 17/702,023

(22) Filed: Mar. 23, 2022

(65) Prior Publication Data

US 2022/0304662 A1  Sep. 29, 2022

Related U.S. Application Data

(60) Provisional application No. 63/165,434, filed on Mar. 24, 2021.

(51) Int. Cl.
*A61B 10/00* (2006.01)
*G01N 33/50* (2006.01)

(52) U.S. Cl.
CPC ............. *A61B 10/00* (2013.01); *G01N 33/50* (2013.01); *A61B 2010/0003* (2013.01)

(58) Field of Classification Search
CPC .... F28D 1/053; F28D 1/05325; F28D 20/021; F28D 2020/0069; F28D 2020/0078;
(Continued)

(56) References Cited

U.S. PATENT DOCUMENTS 4,978,504 A   12/1990  Nason
6,669,908 B2 * 12/2003  Weyker ............... A61B 10/007
                                                        422/417
(Continued)

FOREIGN PATENT DOCUMENTS

CN  109187959 A  1/2019
CN  112304931 A  2/2021

*Primary Examiner* — Jennifer Wecker
*Assistant Examiner* — Jonathan Bortoli
(74) *Attorney, Agent, or Firm* — Christensen, Fonder, Dardi & Herbert PLLC

(57) ABSTRACT

A collection and test device for a rapid test is provided. The device comprises a test fluid accommodation part having a test fluid accommodation space, a test paper accommodation part having a test paper accommodation space, and a collection probe having a channel for the test fluid to flow out from the collection probe. The two ends of the test paper accommodation part are respectively connected to the test fluid accommodation part and the collection probe, and the test paper accommodation space communicates with the channel of the collection probe. The test fluid accommodation space and the test paper accommodation space are separated from each other by a temporary barrier. The temporary barrier can be manually removed or broken to make the test fluid accommodation space communicate with the test paper accommodation space. The device of the present invention can provide the test results conveniently and rapidly.

14 Claims, 4 Drawing Sheets

(58) Field of Classification Search
CPC .......... F28F 2009/0285; F28F 2265/26; F28F 2270/00; F28F 9/02; F28F 9/0246; Y02E 60/14; Y02E 70/30; A61B 10/00; A61B 10/0051; A61B 2010/0003; G01N 33/50; G01N 33/528
See application file for complete search history.

(56) References Cited

U.S. PATENT DOCUMENTS

| | | | |
|---|---|---|---|
| 2013/0109009 A1* | 5/2013 | Kessel | B01L 3/5082 |
| | | | 435/5 |
| 2017/0227536 A1* | 8/2017 | Matsuura | G01N 1/4055 |
| 2018/0259521 A1* | 9/2018 | Kamei | G01N 33/4833 |
| 2019/0250075 A1* | 8/2019 | Wu | A61B 10/0051 |

* cited by examiner

COLLECTION AND TEST DEVICE FOR RAPID TEST

CLAIM FOR PRIORITY

This application claims the benefit of U.S. Patent Provisional Application No. 63/165,434 filed on Mar. 24, 2021, the subject matters of which are incorporated herein in their entirety by reference.

FIELD OF THE INVENTION

The present invention is related to a collection and test device for a rapid test, and more specifically, a collection and test device for a rapid test with a test fluid accommodation part, a test paper accommodation part, and a collection probe.

BACKGROUND OF THE INVENTION

Rapid tests are fast and low in price and thus have been broadly applied in various fields, including disease screening, pregnancy testing, food safety detection, etc. Generally, the test method of a rapid test comprises dipping a collection swab into a sample, mixing the sample on the collection swab with a test fluid, and taking the test fluid with a test paper to obtain a test result. However, the whole test process involves multiple devices, which not only causes inconvenience but also increases the risk of sample contamination. Also, the sample and the test fluid may splash out during operation.

In addition, in the prior art, a test fluid is taken by using a dry test paper, thereby the test fluid must slowly go through a test line onto the test paper via a capillary phenomenon. However, this is relatively slow and needs further improvement to achieve the objective of rapidly providing a test result.

SUMMARY OF THE INVENTION

Therefore, an object of the present invention is to provide a collection and test device for a rapid test, which is convenient to use and can provide the test result rapidly. The collection and test device for a rapid test comprises:
- a test fluid accommodation part having a test fluid accommodation space for accommodating a test fluid;
- a test paper accommodation part having a test paper accommodation space for accommodating a test paper; and
- a collection probe having a channel for the test fluid to flow out from the collection probe, wherein the test paper accommodation part comprises a first end and a second end, wherein the first end of the test paper accommodation part is connected to the test fluid accommodation part and the second end of the test paper accommodation part is connected to the collection probe, and the test paper accommodation space communicates with the channel of the collection probe, and wherein the test fluid accommodation space and the test paper accommodation space are separated from each other by a temporary barrier, and the temporary barrier can be manually removed or broken to make the test fluid accommodation space communicate with the test paper accommodation space.

In some embodiments of the present invention, the temporary barrier, preferably a film, can be broken by applying pressure thereto.

In some embodiments of the present invention, the test paper accommodation part has an opening and an opening cover adapted to close the opening, and the test paper can be placed or removed through the opening.

In some embodiments of the present invention, the test paper accommodation part is made of a transparent material.

In some embodiments of the present invention, the test paper accommodation part has an observation window for observing the test result(s).

In some embodiments of the present invention, the collection and test device for a rapid test further comprises a cap for protecting the collection probe and receiving the test fluid flowing out from the channel of the collection probe.

In some embodiments of the present invention, the test paper is selected from the group consisting of influenza test paper, pregnancy test paper, ovulation test paper, adenovirus test paper, covid test paper, dengue virus test paper, AIDS test paper, parasite test paper, *salmonella* test paper, aflatoxin test paper, *Staphylococcus aureus* test paper, β-adrenergic agonist test paper, antibiotic test paper, pH test paper, pesticide test paper, preservative test paper, melamine test paper, and combinations thereof.

In some embodiments of the present invention, the test fluid is selected from the group consisting of Amies buffer, Dulbecco's phosphate-buffered saline (DPBS), phosphate-buffered saline (PBS), normal saline, trypsin in PBS, borate buffered saline (BBS), Stuart's buffer, and combinations thereof.

To render the above objectives, technical features, and advantages of the present invention more apparent, the present invention will be described in detail with reference to some embodiments hereinafter.

DESCRIPTION OF THE PREFERRED EMBODIMENT

Figure 1:
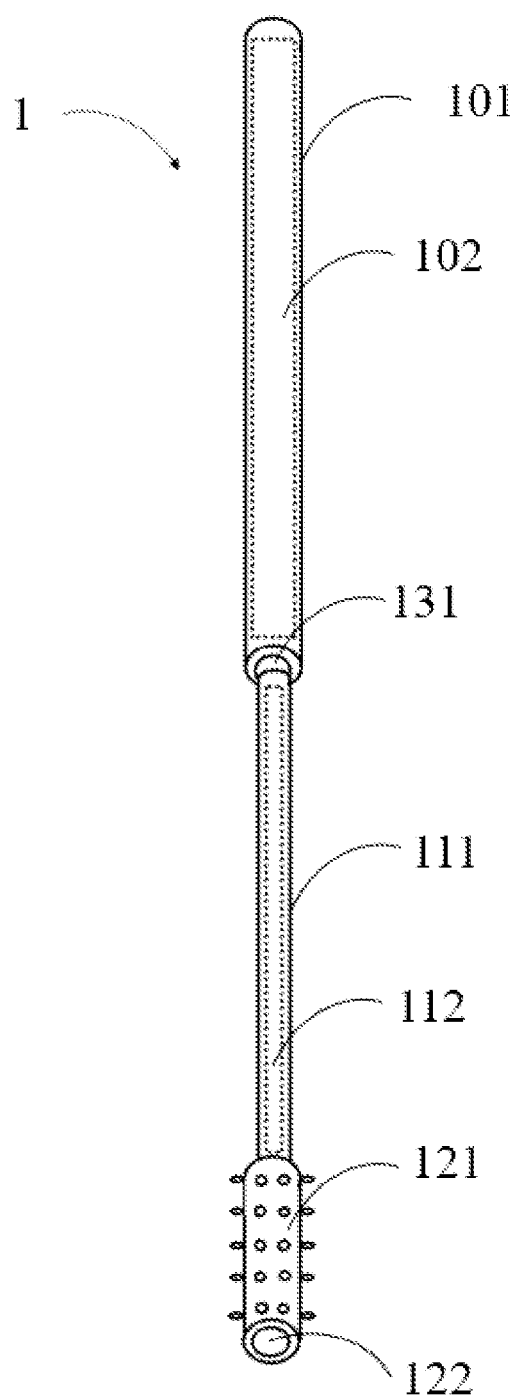
FIG. 1 schematically shows an embodiment of the collection and test device for a rapid test according to the present invention.

The following paragraphs will describe some of the embodiments of the present invention in detail. However, without departing from the spirit of the present invention, the present invention may be embodied in various embodiments and should not be limited to the specific embodiments described in the specification.

In the drawings, the size of elements and regions may be exaggerated for clarity.

Unless it is additionally explained, the expression "a," "an," "the," or the like recited in the specification should include both the singular and plural forms.

As compared to the prior art, the efficacy of the present invention is to provide an improved collection and test device for a rapid test, and the collection and test device for a rapid test has the advantages of being easy to use, having a low risk of sample contamination, and having a low risk of sample splashing during operation. In addition, in the prior art, a test fluid is taken by using a dry test paper, thereby making the test fluid slowly go through a test line on the test paper via a capillary phenomenon. By contrast, in the collection and test device for a rapid test according to the present invention, a test paper is soaked with a test fluid in advance, and then the test fluid with the sample goes through the soaked test paper via diffusion. The speed of diffusion is faster than that of the capillary phenomenon. Therefore, the collection and test device for a rapid test in the present invention can provide a relatively rapid test result. A detailed description of the collection and test device for a rapid tests according to the present invention and the uses thereof is provided below.

FIG. 1 schematically shows an embodiment of the collection and test device for a rapid test according to the present invention. As shown in FIG. 1, the collection and test device 1 for a rapid test comprises: a test fluid accommodation part 101, which has a test fluid accommodation space 102 for accommodating a test fluid; a test paper accommodation part 111, which has a test paper accommodation space 112 for accommodating a test paper; and a collection probe 121, which has a channel 122 for the test fluid to flow out from the collection probe. The test paper accommodation part 111 comprises a first end and a second end, wherein the first end of the test paper accommodation part 111 is connected to the test fluid accommodation part 101 and the second end of the test paper accommodation part 111 is connected to the collection probe 121, and the test paper accommodation space 112 communicates with channel 122 of the collection probe 121. The test fluid accommodation space 102 and the test paper accommodation space 112 are separated from each other by a temporary barrier 131.

Figure 2:
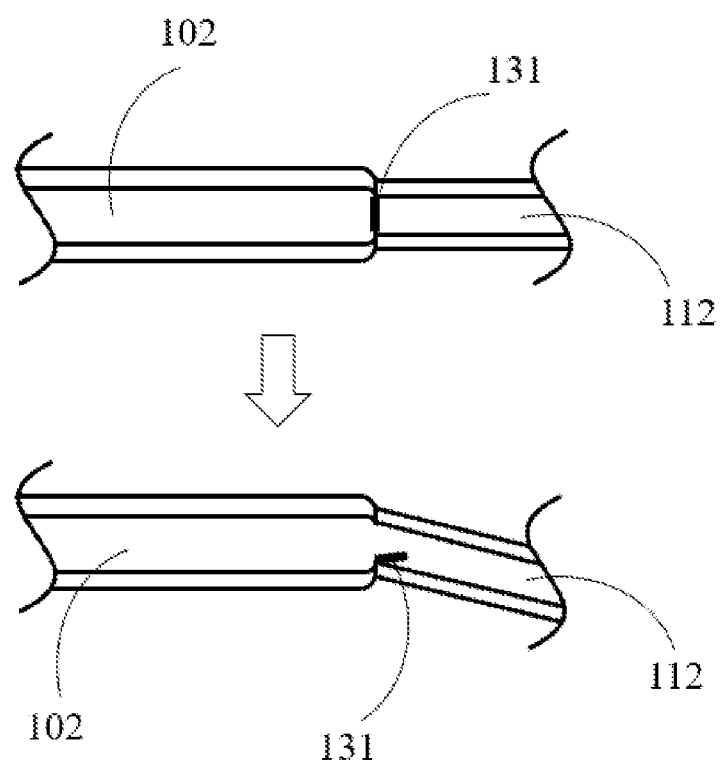
FIG. 2 schematically shows an embodiment of the collection and test device for a rapid test according to the present invention, wherein the temporary barrier of the collection and test device for a rapid test is broken by bending the device.
Figure 3:
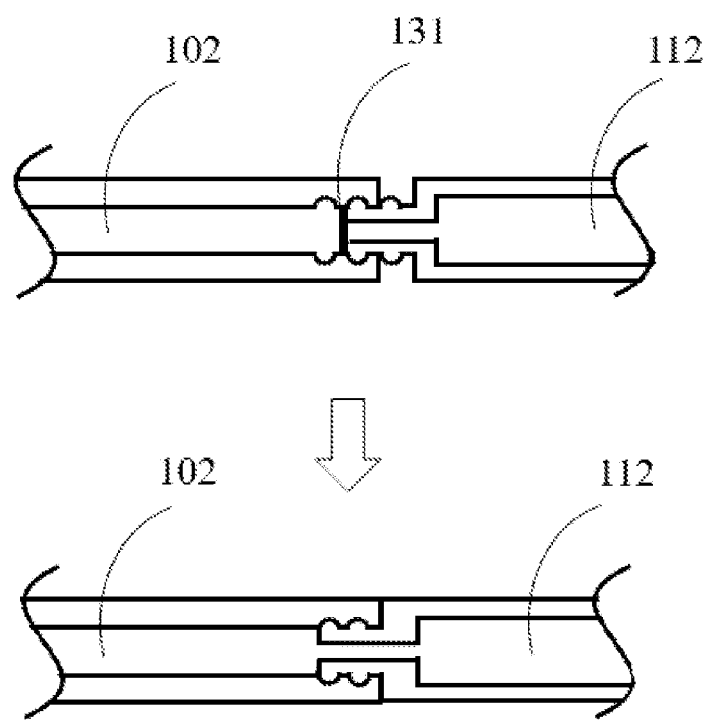
FIG. 3 schematically shows an embodiment of the collection and test device for a rapid test according to the present invention, wherein the temporary barrier of the collection and test device for a rapid test is broken by applying compression along the axis direction of the device.

The temporary barrier 131 can provide a temporary blocking function. The temporary barrier 131 can be manually removed or broken prior to use to make the test fluid accommodation space 102 communicate with the test paper accommodation space 112. FIGS. 2 and 3 schematically show the exemplary design of the temporary barrier. In the embodiment shown in FIG. 2, the temporary barrier 131, such as a film, can be broken by bending the collection and test device for a rapid test to make the test fluid accommodation space 102 communicate with the test paper accommodation space 112. In the embodiment shown in FIG. 3, the temporary barrier 131, such as a film, can be broken by applying compression along the axis direction of the collection and test device for a rapid test to make the test fluid accommodation space 102 communicate with the test paper accommodation space 112. However, the design of the temporary barrier is not limited to the exemplary embodiments. Alternatives can be used by a person having ordinary skill in the art based on the disclosure of the subject specification as well as his/her general knowledge. For example, a person having ordinary skill in the art can change the way for breaking the temporary barrier 131 or use a temporary barrier 131 that can be manually removed.

The shape and size of the test fluid accommodation space 102 are not limited to the embodiment of FIG. 1, but can be changed depending on the needs, as long as the test fluid accommodation space 102 can accommodate the required test fluid. Furthermore, the test fluid can be filled into the test fluid accommodation space 102 during the manufacture of the device or prior to use. Therefore, the test fluid accommodation part 101 can optionally have a filling opening that can be opened for filling test fluid and can be closed when the filling is done.

The shape and size of the test paper accommodation space 112 are not limited to the embodiment of FIG. 1, but can be changed depending on the needs, as long as the test paper accommodation space 112 can accommodate the test paper. Furthermore, the test paper can be placed into the test paper accommodation space 112 during the manufacture of the device or prior to use. Therefore, the test paper accommodation part 111 can optionally have an opening and an opening cover adapted to close the opening, and the test paper can be placed or removed through the opening. The opening or opening cover is preferably provided with a sealing element (e.g., a gasket) to improve leak proofness.

In addition, the test paper accommodation part 111 is preferably made of a transparent material or has an observation window for observing test result(s), such as a transparent window, in terms of convenience in observation of test result(s).

The shape and size of the collection probe 121 are not particularly limited, as long as the collection probe can perform sample collection. The surface of collection probe 121 preferably has one or more protrusion(s) to improve the efficiency of sample collection. The size of the channel 122 of the collection probe 121 is not particularly limited, as long as the channel 122 can provide sufficient space for the test fluid to pass through.

Figure 4:
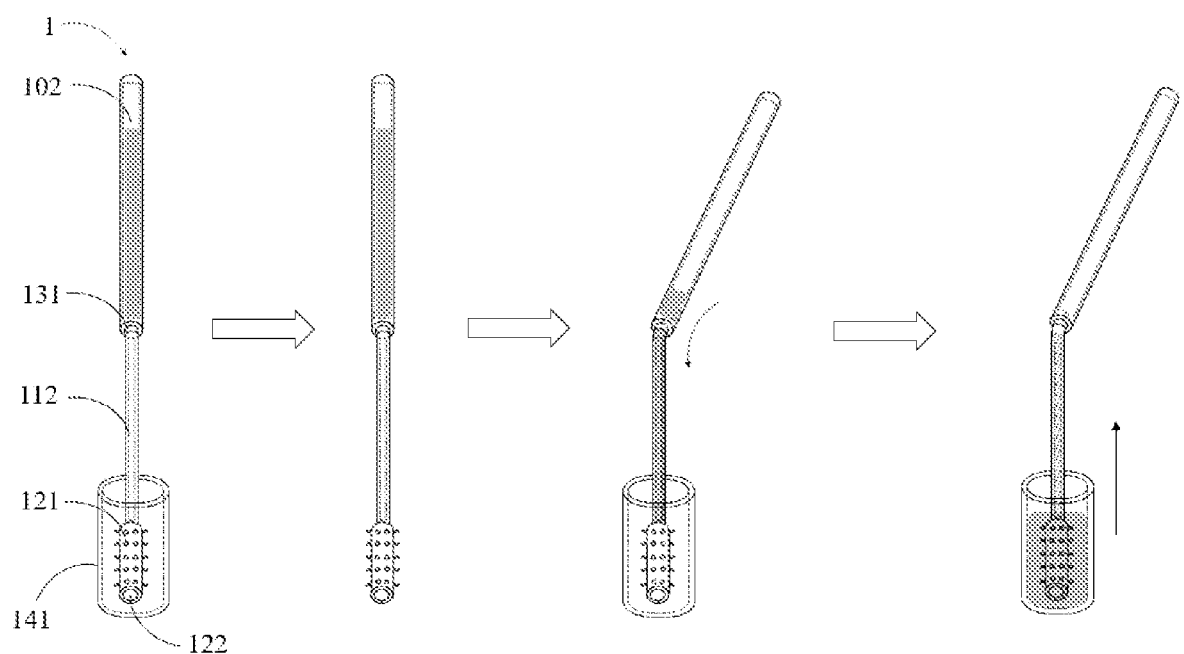
FIG. 4 schematically shows a test process of using the collection and test device for a rapid test as shown in FIG. 1.

FIG. 4 schematically shows a test process of using the collection and test device for a rapid test according to the present invention. As shown in FIG. 4, in addition to the aforesaid elements, the collection and rapid device 1 for a rapid test can have a cap 141. When the device is not in use, the collection probe 121 is placed in the cap 141 to prevent contamination. Furthermore, the test fluid is sealed in the test fluid accommodation space 102 by the temporary barrier 131. A user can remove the cap 141 prior to use and expose the collection probe 121 to conduct a sample collection. After the sample collection is done, the collection probe 121 is placed into the cap 141 again, and the temporary barrier 131 is broken by bending the test fluid accommodation part 101 and the test paper accommodation part 111 to make the test fluid accommodation space 102 communicate with the test paper accommodation space 112, thereby allowing the test fluid flows from the test fluid accommodation space 102 to the test paper accommodation space 112 and wetting the test paper placed in the test paper accommodation space 112. Afterward, the test fluid flows out from the channel 122 of the collection probe 121 that is communicated with the test paper accommodation space 112 and received in the cap 141. The test fluid is mixed with the collected sample in the cap 141, and moves back to the test paper via diffusion, thereby showing the test result(s).

In the collection and test device for a rapid test according to the present invention, the types of test fluid and test paper are not particularly limited and can be chosen depending on the item(s) to be tested. The test fluid usually contains such as salts, carbohydrates, proteins, or electrolytes, and thus can be a buffer, a reactive solution, or a combination thereof. Examples of the test fluid include but are not limited to Amies buffer, Dulbecco's phosphate buffered saline (DPBS), phosphate buffered saline (PBS), normal saline, trypsin in PBS, borate buffered saline (BBS), and Stuart's buffer, and the listed test fluids can be used alone or in any combination. The test paper usually uses antibodies, antigens, haptens, small molecules, nucleic acids, aptamer molecules or chemical compounds as test target together with nanomaterial to provide coloration result(s), thereby achieving the test purpose. Examples of the test paper include but are not limited to influenza test paper (e.g., influenza A test paper, influenza B test paper), pregnancy test paper, ovulation test paper, adenovirus test paper, covid test paper, dengue virus test paper, AIDS test paper, parasite test paper, salmonella test paper, aflatoxin test paper, *Staphylococcus aureus* test paper, β-adrenergic agonist test paper, antibiotic test paper, pH test paper, pesticide test paper, preservative test paper, and melamine test paper, and the listed test papers can be used alone or in any combination.

The material of the collection and test device for a rapid test according to the present invention is not particularly limited, which includes but is not limited to plastics, rubbers, glasses, metals, ceramics, etc. However, the collection and test device for a rapid test is preferably made of plastics in terms of costs. Examples of plastics include but are not limited to acrylonitrile butadiene styrene (ABS), polyethylene (PE), polypropylene (PP), polyvinylchloride (PVC), photosensitive resin, polyethylene terephthalate (PETG), and polylactic acid (PLA), and the listed plastics can be used alone or in any combination.

The collection and rapid device for a rapid test according to the present invention can be made by using any known method. For example, the collection and rapid device for a rapid test can be formed in one piece or by assembling the related elements which are separately produced. In the case of using plastics as a material, the collection and rapid device for a rapid test can be made by 3D printing, injection molding, blow molding, compression molding, casting, etc. In some embodiments of the present invention, the collection and rapid device for a rapid test is made by 3D printing.

The above example is used to illustrate the inventive features of the present invention but does not limit the scope of the present invention. People skilled in this field may proceed with a variety of modifications and replacements without departing from the principle and spirit thereof, and thus shall belong to the scope as claimed in the present invention. Therefore, the scope of protection of the present invention is that as defined in the claims as appended.

What is claimed is:

1. A collection and test device for a rapid test, comprising:
   a test fluid accommodation part having a test fluid accommodation space for accommodating a test fluid;
   a test paper accommodation part having a test paper accommodation space for accommodating a test paper; and
   a collection probe for collecting a sample, which has a channel for the test fluid to flow out from the collection probe,
   wherein the test paper accommodation part comprises a first end and a second end, wherein the first end of the test paper accommodation part is connected to the test fluid accommodation part and the second end of the test paper accommodation part is connected to the collection probe, and the test paper accommodation space communicates with the channel of the collection probe, and wherein the test paper accommodation part is between the test fluid accommodation part and the collection probe, and
   wherein the test fluid accommodation space and the test paper accommodation space are separated from each other by a temporary barrier, and the temporary barrier can be manually removed or broken to make the test fluid accommodation space communicate with the test paper accommodation space, enabling the test fluid to first wet the test paper, thus subsequently enabling the test fluid with the collected sample to diffuse through the test paper.

2. The collection and test device for a rapid test as claimed in claim 1, wherein the temporary barrier can be broken by applying pressure thereto.

3. The collection and test device for a rapid test as claimed in claim 2, wherein the temporary barrier is a film.

4. The collection and test device for a rapid test as claimed in claim 1, wherein the test paper accommodation part has an opening and an opening cover adapted to close the opening, and the test paper can be placed or removed through the opening.

5. The collection and test device for a rapid test as claimed in claim 2, wherein the test paper accommodation part has an opening and an opening cover adapted to close the opening, and the test paper can be placed or removed through the opening.

6. The collection and test device for a rapid test as claimed in claim 3, wherein the test paper accommodation part has an opening and an opening cover adapted to close the opening, and the test paper can be placed or removed through the opening.

7. The collection and test device for a rapid test as claimed in claim 1, wherein the test paper accommodation part is made of a transparent material.

8. The collection and test device for a rapid test as claimed in claim 2, wherein the test paper accommodation part is made of a transparent material.

9. The collection and test device for a rapid test as claimed in claim 3, wherein the test paper accommodation part is made of a transparent material.

10. The collection and test device for a rapid test as claimed in claim 1, further comprising a cap for protecting the collection probe and receiving the test fluid flowing out from the channel of the collection probe.

11. The collection and test device for a rapid test as claimed in claim 2, further comprising a cap for protecting the collection probe and receiving the test fluid flowing out from the channel of the collection probe.

12. The collection and test device for a rapid test as claimed in claim 3, further comprising a cap for protecting the collection probe and receiving the test fluid flowing out from the channel of the collection probe.

13. The collection and test device for a rapid test as claimed in claim 1, further comprising the test paper, wherein the test paper is selected from the group consisting of an influenza test paper, a pregnancy test paper, an ovulation test paper, an adenovirus test paper, a covid test paper, a dengue virus test paper, an acquired immunodeficiency syndrome (AIDS) test paper, a parasite test paper, a salmonella test paper, an aflatoxin test paper, a *Staphylococcus aureus* test paper, a β-adrenergic agonist test paper, an antibiotic test paper, a pH test paper, a pesticide test paper, a preservative test paper, a melamine test paper, and a combination thereof.

14. The collection and test device for a rapid test as claimed in claim 1, wherein the test fluid is selected from the group consisting of an Amies buffer, a Dulbecco's phosphate buffered saline (DPBS), a phosphate buffered saline (PBS), a normal saline, a trypsin in PBS, a borate buffered saline (BBS), a Stuart's buffer, and a combination thereof.

* * * * *